(12) United States Patent
Kuiper et al.

(10) Patent No.: US 10,815,532 B2
(45) Date of Patent: *Oct. 27, 2020

(54) CLASSIFIER FOR THE MOLECULAR CLASSIFICATION OF MULTIPLE MYELOMA

(71) Applicant: Erasmus University Medical Center Rotterdam, Rotterdam (NL)

(72) Inventors: Rowan Kuiper, Rotterdam (NL); Pieter Sonneveld, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 3 days.

This patent is subject to a terminal disclaimer.

(21) Appl. No.: 15/959,703

(22) Filed: Apr. 23, 2018

(65) Prior Publication Data

US 2018/0237866 A1    Aug. 23, 2018

Related U.S. Application Data

(63) Continuation of application No. 14/232,176, filed as application No. PCT/EP2012/063722 on Jul. 12, 2012, now Pat. No. 9,976,185.

(30) Foreign Application Priority Data

Jul. 14, 2011    (EP) .................................... 11173971

(51) Int. Cl.
*C12Q 1/6886*    (2018.01)
*C12Q 1/6837*    (2018.01)

(52) U.S. Cl.
CPC ......... *C12Q 1/6886* (2013.01); *C12Q 1/6837* (2013.01); *C12Q 2600/112* (2013.01); *C12Q 2600/118* (2013.01); *C12Q 2600/158* (2013.01)

(58) Field of Classification Search
CPC ................ C12Q 1/6886; C12Q 1/6837; C12Q 2600/112; C12Q 2600/118; C12Q 2600/158; C12Q 1/6813
See application file for complete search history.

(56) References Cited

U.S. PATENT DOCUMENTS

| | | | |
|---|---|---|---|
| 2003/0175753 A1* | 9/2003 | Shaughnessy | C12Q 1/6886 435/6.14 |
| 2007/0093969 A1 | 4/2007 | Mendrick et al. | |
| 2008/0187930 A1* | 8/2008 | Shaughnessy | C12Q 1/6886 435/6.14 |
| 2008/0274911 A1 | 11/2008 | Burington et al. | |
| 2014/0221313 A1 | 8/2014 | Kuiper et al. | |

FOREIGN PATENT DOCUMENTS

| | | |
|---|---|---|
| EP | 1964930 A1 | 9/2008 |
| WO | 2010064016 A2 | 6/2010 |
| WO | 2010151731 A1 | 12/2010 |
| WO | 2013007795 A1 | 1/2013 |

OTHER PUBLICATIONS

Palmer et al. BMC Genomics. 2006. 7:115. (Year: 2006).*
Saito-Hisaminato et al. DNA Research. 2002. 9:35-45. (Year: 2002).*
Ehrhardt et al. J.Exp.Med. 2008. 205(8):1807-1817. (Year: 2008).*
Gutierrez et al. Leukemia. 2007. 21:541-549. (Year: 2007).*
Ong et al. Experimental Hematology. 2006. 34(6): 713-720. (Year: 2006).*
Hata et al. Blood. 1993. 81(12):3357-3364. (Year: 1993).*
Bair et al., Prediction by Supervised Principal Components, Journal of the American Statistical Association, Mar. 2006, pp. 119-137, vol. 101, No. 473.
Bolstad et al., A comparison of normalization methods fro high density oligonucleotide array data based on variance and bias, Bioinformatics, 2003, pp. 185-193, vol. 19, No. 2.
Broyl et al., Gene expression profiling for molecular classification fo multiple myeloma in newly diagnosed patients, Blood, 2010, pp. 2543-2553, vol. 116, No. 14.
Chng et al., Molecular dissection of hyperdiploid Multiple Myeloma by Gene Expression Profiling, Cancer Res, 2007, pp. 2982-2989, vol. 67, No. 7.
Chng et al., Translocation t(4;14) retains prognostic significance even in the setting of high-risk molecular signature, Leukemia, 2008, pp. 459-461, vol. 22, doi:10.1038/sj.leu.2404934; published online Sep. 6, 2007.
Chou et al., Optimization of probe length and the number of probes per gene for optimal microarray analysis of gene expression, Nucleic Acids Research, 2004, 8 pages, vol. 32, No. 12.
Communication from European Patent Office for Patent Application No. 12 733 765.7 dated Dec. 5, 2014.
Decaux et al., "Prediction of survival in multiple myeloma based on gene expression profiles reveals cell cycle and chromosomal instability signatures in high-risk patients and hyperdiploid signatures in low-risk patients: a study of the Intergroupe Francophone du Myélome," Journal of Clinical Oncology, vol. 26, No. 29, Oct. 10, 2008, pp. 4798-4805.
Dickens et al., Homozygous Deletion Mapping in Myeloma Samples Identifies Genes and an Expression Signature Relevant to Pathogenesis and Outcome, Clin Cancer Res., Mar. 2010, pp. 1856-1864, vol. 16, No. 6.
Eleveld-Trancikova et al, Translocation t(4;14) retains prognostic significance even in the setting of high-risk molecular signature, Leukemia, Sep. 6, 2007, 22, pp. 459-461.
International Search Report and Written Opinion for International Application No. PCT/EP2012/063722, dated Nov. 8, 2012, 12 pages.

(Continued)

*Primary Examiner* — Joseph G. Dauner
(74) *Attorney, Agent, or Firm* — TraskBritt

(57) ABSTRACT

This disclosure is in the field of molecular diagnostics and relates to a method for classifying samples obtained from patients diagnosed with multiple myeloma into three newly defined clusters. The disclosure also relates to a method for determining the prognosis of an individual diagnosed with multiple myeloma as well as a method for the prediction of the response to treatment of an individual diagnosed with multiple myeloma. More in particular, the disclosure provides a method for determining the disease outcome or the prognosis of a patient diagnosed with multiple myeloma by classifying said patient into a high risk or a low risk category, based on a 92-gene classifier.

1 Claim, 5 Drawing Sheets

(56) References Cited

OTHER PUBLICATIONS

Michiels et al., Prediction of cancer outcome with microarrays: a multiple random validation strategy, Lancet., 2005, pp. 488-492, vol. 365.
Moreau et al., Proteasome inhibitors in multiple myeloma: 10 years later, Blood, 2012, pp. 947-959, vol. 120, No. 5.
PCT International Preliminary Report on Patentability, PCT/EP2012/063722 dated Jan. 14, 2014.
Rapaport et al., Comprehensive evaluation of differential gene expression analysis methods for RNA-seq data, Genome Biology, 2013, 14:R95.
Shaughnessy Jr., et al., A validated gene expression model of high risk multiple myeloma is defined by deregulated expression of genes mapping to chromosome 1, Blood, Mar. 15, 2007, pp. 2276-2284, vol. 109, The American Society of Hematology, Washington DC.
Slonim, D.J., From patterns to pathways: gene expression data analysis comes of age, Nature Genetics Supplement, Dec. 2002, pp. 502-508, vol. 32.
Zhan et al., The molecular classification of multiple myeloma, Blood, 2006, pp. 2020-2028, vol. 108, No. 6.
International Search Report for International Application No. PCT/EP12/063722, dated Nov. 8, 2012, 4 pages.
International Written Opinion for International Application No. PCT/EP2012/063722, dated Nov. 8, 2012, 7 pages.
Japanese Notice of Reasons for Refusal for Japanese Application No. 2014-519565, dated Jun. 23, 2016, 7 pages with English Translation.
European Search and Opinion for European Application No. 11173971, dated Mar. 7, 2012, 6 pages.
Japanese Written Opinion for Japanese Application No. 2014-519565, dated Aug. 16, 2016, 8 pages with English Translation.

* cited by examiner

CLASSIFIER FOR THE MOLECULAR CLASSIFICATION OF MULTIPLE MYELOMA

CROSS-REFERENCE TO RELATED APPLICATIONS

This application is a continuation of co-pending U.S. patent application Ser. No. 14/232,176, filed Mar. 19, 2014, which is a national phase entry under 35 U.S.C. § 371 of International Patent Application PCT/EP2012/063722, filed Jul. 12, 2012, designating the United States of America and published in English as International Patent Publication WO 2013/007795 A1 on Jan. 17, 2013, which claims the benefit under Article 8 of the Patent Cooperation Treaty to European Patent Application Serial No. 11173971.0, filed Jul. 14, 2011.

TECHNICAL FIELD

This application is in the field of molecular diagnostics and relates to a method for classifying samples obtained from patients diagnosed with multiple myeloma. The application also relates to a method for determining the prognosis of an individual diagnosed with multiple myeloma as well as a method for the prediction of the response to treatment of an individual diagnosed with multiple myeloma.

BACKGROUND

Multiple myeloma (MM) is characterized by accumulation of malignant monoclonal plasma cells in the bone marrow. Median overall survival (OS) is 3 to 4 years but varies widely between patients. Currently, the International Staging System (ISS), based on serum β2m and albumin is clinically widely used to classify MM patients into three prognostic categories.[1]

Based on cytogenetics, two classes of MM can be distinguished with implications for MM biology and prognosis. Hyperdiploid MM, ~60% of patients, characterized by trisomies of multiple odd chromosomes (3, 5, 7, 9, 11, 15, 19, and 21) has a relatively good prognosis. Non-hyperdiploid MM, ~40% of cases, is characterized by recurrent translocations involving the immunoglobulin heavy chain gene at 14q32, resulting in transcriptional activation of CCND1, CCND3, MAF, MAFB, or FGFR3/MMSET.[2, 3] Translocation t(11;14), involving CCND1, confers a relatively favorable prognosis whereas translocation t(4;14), involving FGFR3 and MMSET, has poor prognosis.[4, 5] The translocations t(14;16) and t(14;20), involving the MAF oncogenes also confer a poor prognosis, although recently this has been debated.[6] In addition, del(17p), del(13q) and 1q-gain detected with conventional karyotyping were reported to be associated with poor prognosis.[7]

Based on gene expression analysis, a number of classifications for MM have been published, which include the University of Arkansas for Medical Sciences (UAMS) classification and, more recently, a classification by our own group. The UAMS molecular classification of myeloma consists of seven distinct gene expression clusters, including translocation clusters MS, MF, and CD-1/2, as well as a hyperdiploid cluster (HY), a cluster with proliferation-associated genes (PR), and a cluster characterized by low percentage of bone disease (LB).[8] Our classification of MM resulted in three additional clusters: NFκB, CTA and PRL3.[9]

Gene expression is able to explain an even larger amount of variance in survival compared to ISS and cytogenetics. One of the first survival signatures based on gene expression was the UAMS-70-gene classifier, and the further refined UAMS-17-gene classifier.[10, 11] Other classifiers include the Millennium signature, the MRC-IX-6-gene signature, and the IFM classifier.[12-14] In addition, signatures were reported to predict plasma cell proliferation such as the recently published gene expression proliferation index (GPI).[15]

The aim of this study was to develop a prognostic signature, based upon gene expression profiles (GEPs) of MM patients, treated with either standard induction treatment or bortezomib induction, followed in both cases by high-dose melphalan and maintenance.

BRIEF SUMMARY

Presented herein is a classifier comprising a 92-gene set capable of distinguishing between patients with a high risk and patients with a low risk. In a survival analysis of newly diagnosed multiple myeloma (MM) patients, the classifier yielded excellent results wherein the classification in the low risk group identified patients with a good overall survival, whereas the group identified as high risk showed significantly worse overall survival rates.

The disclosure, therefore, relates to a method for determining the disease outcome or the prognosis of a patient diagnosed with multiple myeloma by classifying the patient into a high risk or a low risk category, the method comprising the steps of:
a) providing a gene chip comprising probes for the detection of at least the 92-gene set according to Table 1,
b) contacting the gene chip with a sample comprising mRNA from a patient,
c) determining the expression levels of the 92-gene set in the sample,
d) normalizing the expression levels using mean/variance normalization in order to obtain the normalized expression value,
e) multiplying the normalized expression value with the beta value according to Table 1 to obtain the calculated value for an individual probe,
f) determining an EMC-92 score by summation of the calculated values of the individual probes, wherein an EMC-92 score above a predetermined threshold indicates that the patient is to be classified in the high risk category and a score at or below the predetermined threshold indicates that the patient is to be classified in the low risk category.

BRIEF DESCRIPTION OF THE DRAWINGS

FIG. 1A: UAMS Total Therapy 2; FIG. 1B: UAMS Total Therapy 3; FIG. 1C: MRC-IX; and FIG. 1D: APEX.

DETAILED DESCRIPTION

Figure 1A:
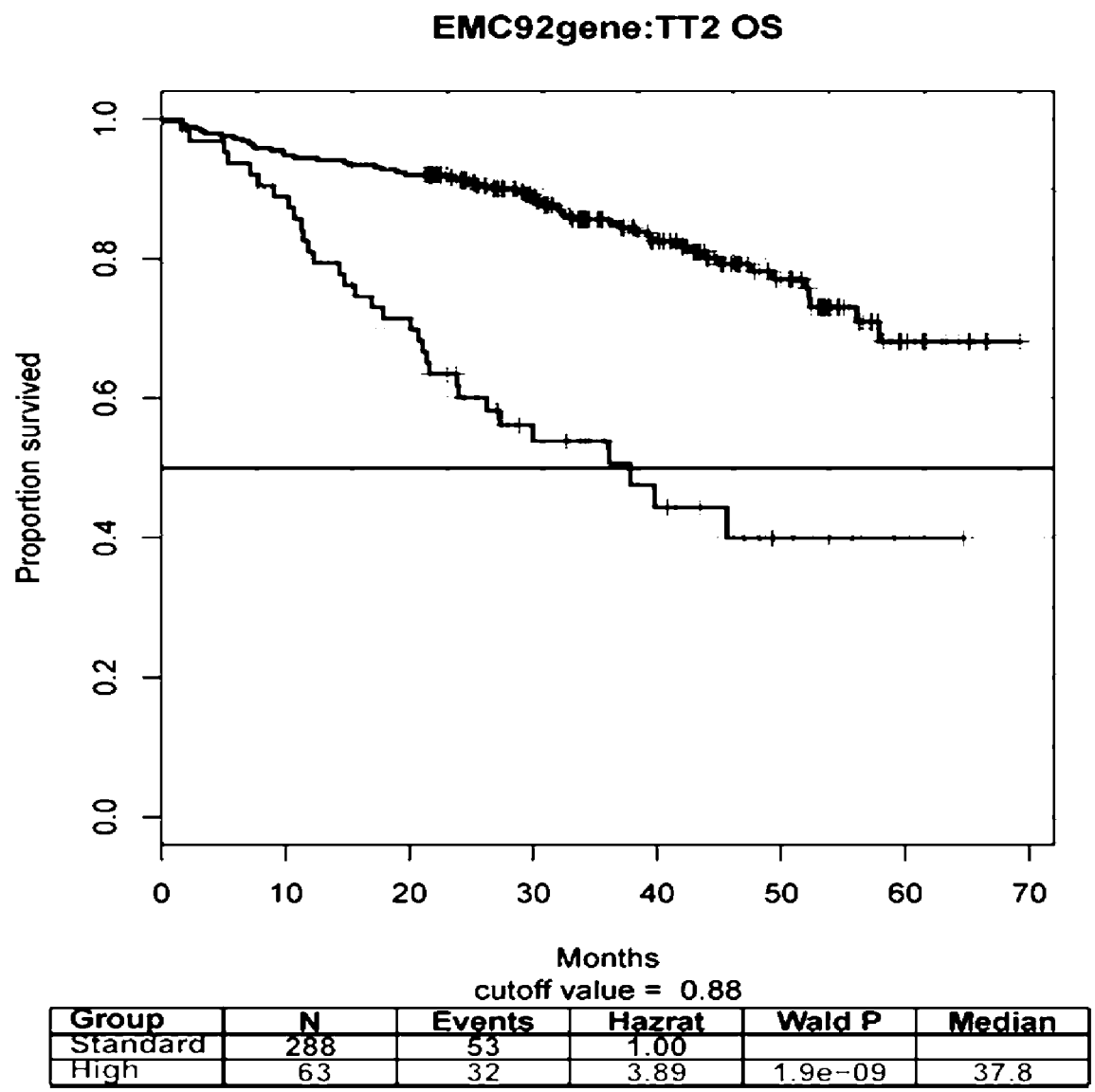
FIGS. 1A-1D: Performance of the EMC-92 classifier in predicting overall survival. High risk signature on four validation sets with a fixed cut-off value of 0.827.

A classifier comprising a 92-gene set capable of distinguishing between patients with a high risk and patients with a low risk is disclosed herein. In a survival analysis of newly diagnosed multiple myeloma (MM) patients, the classifier yielded excellent results wherein the classification in the low risk group identified patients with a good overall survival, whereas the group identified as high risk showed significantly worse overall survival rates.

The classifier was validated in an experimental setting wherein patients with poor overall survival (OS) were distinguished from patients with standard OS. Therefore, an SPCA model was built using the HOVON65/GMMG-HD4 data as a training set (see the experimental section below). A number of 1088 probe sets were found to be associated with progression-free survival (PFS) in a univariate Cox regression analysis (FDR <10%). Based on these probe sets, a classifier with 92 probe sets was developed (Table 1). This classifier will be termed the EMC-92-gene signature.

TABLE 1

| # | Probes | Beta | Gene | Chromosome | Band |
|---|---|---|---|---|---|
| 1 | 226217_at | −0.0319 | SLC30A7 | 1 | p21.2 |
| 2 | 208967_s_at | 0.0113 | AK2 | 1 | p35.1 |
| 3 | 202553_s_at | 0.0054 | SYF2 | 1 | p36.11 |
| 4 | 217728_at | 0.0773 | S100A6 | 1 | q21.3 |
| 5 | 223381_at | −0.0070 | NUF2 | 1 | q23.3 |
| 6 | 218365_s_at | 0.0035 | DARS2 | 1 | q25.1 |
| 7 | 211963_s_at | 0.0303 | ARPC5 | 1 | q25.3 |
| 8 | 222680_s_at | 0.0205 | DTL | 1 | q32.3 |
| 9 | 221826_at | 0.0200 | ANGEL2 | 1 | q32.3 |
| 10 | 201795_at | 0.0067 | LBR | 1 | q42.12 |
| 11 | 202813_at | 0.0548 | TARBP1 | 1 | q42.2 |
| 12 | 202322_s_at | 0.0129 | GGPS1 | 1 | q42.3 |
| 13 | 202728_s_at | −0.1105 | LTBP1 | 2 | p22.3 |
| 14 | 209683_at | −0.0561 | FAM49A | 2 | p24.2 |
| 15 | 201930_at | −0.0090 | MCM6 | 2 | q21.3 |
| 16 | 228416_at | −0.0778 | ACVR2A | 2 | q22.3 |
| 17 | 206204_at | 0.0477 | GRB14 | 2 | q24.3 |
| 18 | 215177_s_at | −0.0768 | ITGA6 | 2 | q31.1 |
| 19 | 224009_x_at | −0.0520 | DHRS9 | 2 | q31.1 |
| 20 | AFFX-HUMISGF3A/M97935_MA_at | 0.0525 | STAT1 | 2 | q32.2 |
| 21 | 222154_s_at | 0.0154 | SPATS2L | 2 | q33.1 |
| 22 | 207618_s_at | 0.0746 | BCS1L | 2 | q35 |
| 23 | 239054_at | −0.1088 | SFMBT1 | 3 | p21.1 |
| 24 | 217852_s_at | 0.0008 | ARL8B | 3 | p26.1 |
| 25 | 219510_at | −0.0097 | POLQ | 3 | q13.33 |
| 26 | 202107_s_at | 0.0225 | MCM2 | 3 | q21.3 |
| 27 | 220351_at | 0.0420 | CCRL1 | 3 | q22.1 |
| 28 | 208942_s_at | −0.0997 | SEC62 | 3 | q26.2 |
| 29 | 233437_at | 0.0446 | GABRA4 | 4 | p12 |
| 30 | 225366_at | 0.0140 | PGM2 | 4 | p14 |
| 31 | 218662_s_at | −0.0176 | NCAPG | 4 | p15.31 |
| 32 | 204379_s_at | 0.0594 | FGFR3 | 4 | p16.3 |
| 33 | 201307_at | 0.0165 | SEPT11 | 4 | q21.1 |
| 34 | 202542_s_at | 0.0870 | AIMP1 | 4 | q24 |
| 35 | 205046_at | 0.0087 | CENPE | 4 | q24 |
| 36 | 226218_at | −0.0644 | IL7R | 5 | p13.2 |
| 37 | 202532_s_at | −0.0006 | DHFR | 5 | q14.1 |
| 38 | 226742_at | −0.0345 | SAR1B | 5 | q31.1 |
| 39 | 231738_at | 0.0686 | PCDHB7 | 5 | q31.3 |
| 40 | 214150_x_at | −0.0349 | ATP6V0E1 | 5 | q35.1 |
| 41 | 201555_at | −0.0052 | MCM3 | 6 | p12.2 |
| 42 | 209026_s_at | 0.0255 | TUBB | 6 | p21.33 |
| 43 | 211714_x_at | 0.0221 | TUBB | 6 | p21.33 |
| 44 | 213002_at | −0.0418 | MARCKS | 6 | p22.2 |
| 45 | 221041_s_at | −0.0520 | SLC17A5 | 6 | q13 |
| 46 | 217824_at | −0.0041 | NCUBE1 | 6 | q15 |
| 47 | 223811_s_at | 0.0556 | SUN1/GET4 | 7 | p22.3 |
| 48 | 202842_s_at | −0.0626 | DNAJB9 | 7 | q31.1 |
| 49 | 208232_x_at | −0.0493 | Unknown | 8 | p12 |
| 50 | 208732_at | −0.0618 | RAB2A | 8 | q12.1 |
| 51 | 201398_s_at | −0.0254 | TRAM1 | 8 | q13.3 |
| 52 | 233399_x_at | −0.0184 | ZNF252 | 8 | q24.3 |
| 53 | 200775_s_at | 0.0163 | HNRNPK | 9 | q21.32 |
| 54 | 230034_x_at | −0.0330 | MRPL41 | 9 | q34.3 |
| 55 | 204026_s_at | 0.0046 | ZWINT | 10 | q21.1 |

TABLE 1-continued

| # | Probes | Beta | Gene | Chromosome | Band |
|---|---|---|---|---|---|
| 56 | 243018_at | 0.0407 | Unknown | 11 | p14.1 |
| 57 | 222713_s_at | 0.0278 | FANCF | 11 | p14.3 |
| 58 | 221755_at | 0.0396 | EHBP1L1 | 11 | q13.1 |
| 59 | 231210_at | 0.0093 | C11orf85 | 11 | q13.1 |
| 60 | 202884_s_at | 0.0714 | PPP2R1B | 11 | q23.1 |
| 61 | 219550_at | 0.0559 | ROBO3 | 11 | q24.2 |
| 62 | 238780_s_at | −0.0529 | Unknown | 11 | q24.3 |
| 63 | 208747_s_at | −0.0874 | C1S | 12 | p13.31 |
| 64 | 38158_at | 0.0423 | ESPL1 | 12 | q13.13 |
| 65 | 217732_s_at | −0.0252 | ITM2B | 13 | q14.2 |
| 66 | 214482_at | 0.0861 | ZBTB25 | 14 | q23.3 |
| 67 | 200701_at | −0.0210 | NPC2 | 14 | q24.3 |
| 68 | 238662_at | 0.0490 | ATPBD4 | 15 | q14 |
| 69 | 217548_at | −0.0423 | C15orf38 | 15 | q26.1 |
| 70 | 213007_at | −0.0106 | FANCI | 15 | q26.1 |
| 71 | 231989_s_at | 0.0730 | SMG1 | 16 | p12.3 |
| 72 | 238116_at | 0.0661 | DYNLRB2 | 16 | q23.2 |
| 73 | 212282_at | 0.0530 | TMEM97 | 17 | q11.2 |
| 74 | 203145_at | −0.0002 | SPAG5 | 17 | q11.2 |
| 75 | 201292_at | −0.0372 | TOP2A | 17 | q21.2 |
| 76 | 210334_x_at | 0.0175 | BIRC5 | 17 | q25.3 |
| 77 | 212055_at | 0.0384 | C18orf10 | 18 | q12.2 |
| 78 | 242180_at | −0.0585 | TSPAN16 | 19 | p13.2 |
| 79 | 208904_s_at | −0.0334 | RPS28 | 19 | p13.2 |
| 80 | 213350_at | 0.0056 | RPS11 | 19 | q13.3 |
| 81 | 200855_s_at | 0.0437 | NOP56 | 20 | p13 |
| 82 | 212788_x_at | −0.0164 | FTL | 19 | p13 |
| 83 | 215181_at | −0.0342 | CDH22 | 20 | q13.12 |
| 84 | 221677_s_at | 0.0126 | DONSON | 21 | q22.11 |
| 85 | 201102_s_at | 0.0349 | PFKL | 21 | q22.3 |
| 86 | 208667_s_at | −0.0390 | ST13 | 22 | q13.2 |
| 87 | 216473_x_at | −0.0576 | DUX4 | 4/10 | q35.2/q26.3 |
| 88 | 200933_x_at | −0.0323 | RPS4X | X | q13.1 |
| 89 | 218355_at | 0.0116 | KIF4A | X | q13.1 |
| 90 | 221606_s_at | 0.0208 | HMGN5 | X | q21.1 |
| 91 | 225601_at | 0.0750 | HMGB3 | X | q28 |
| 92 | 214612_x_at | 0.0496 | MAGEA6 | X | q28 |

Figure 1B:
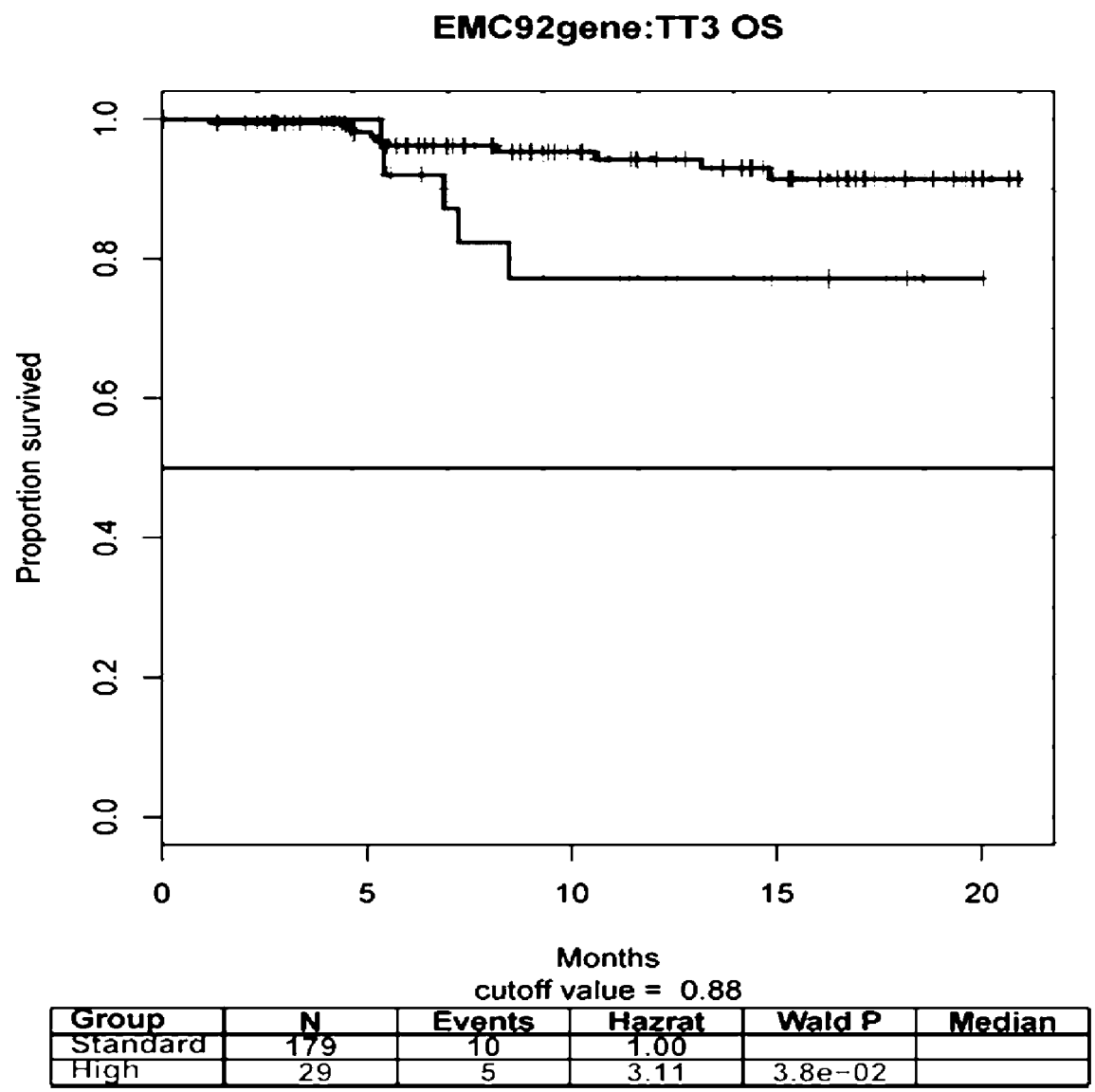
Figure 1C:
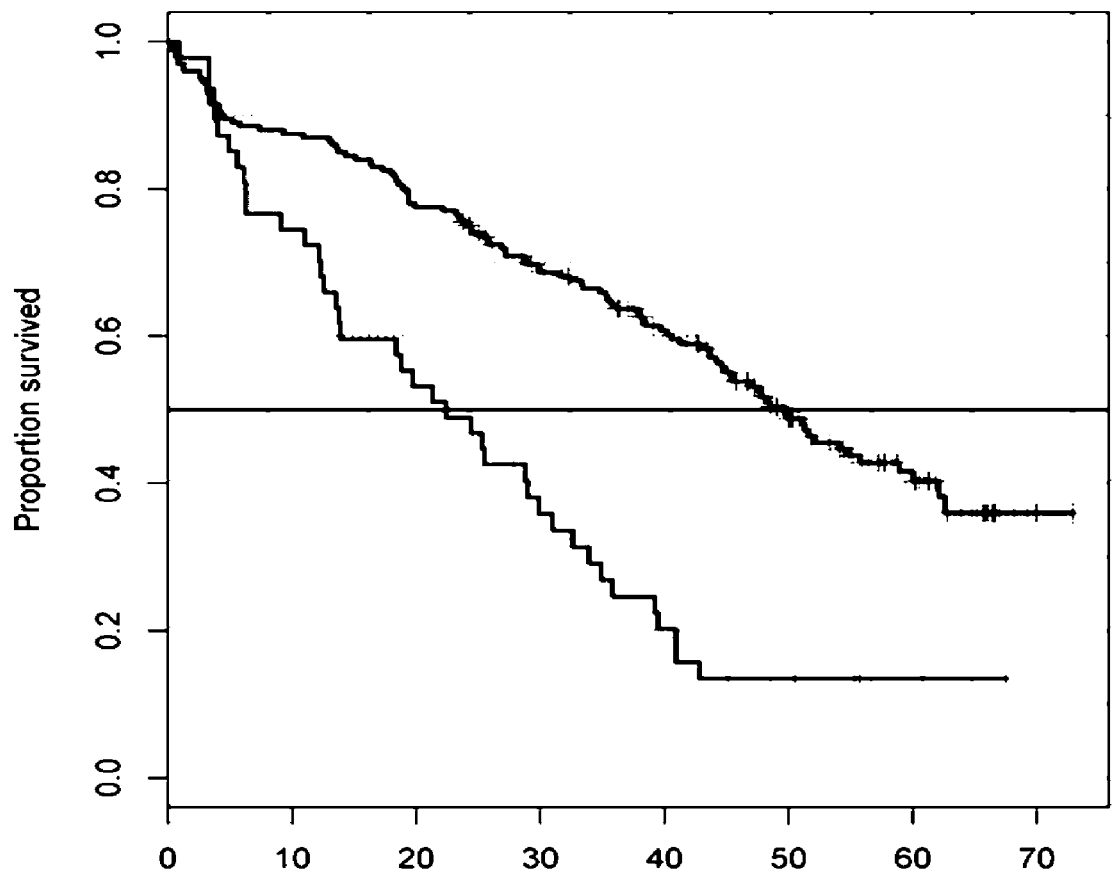
Figure 1D:
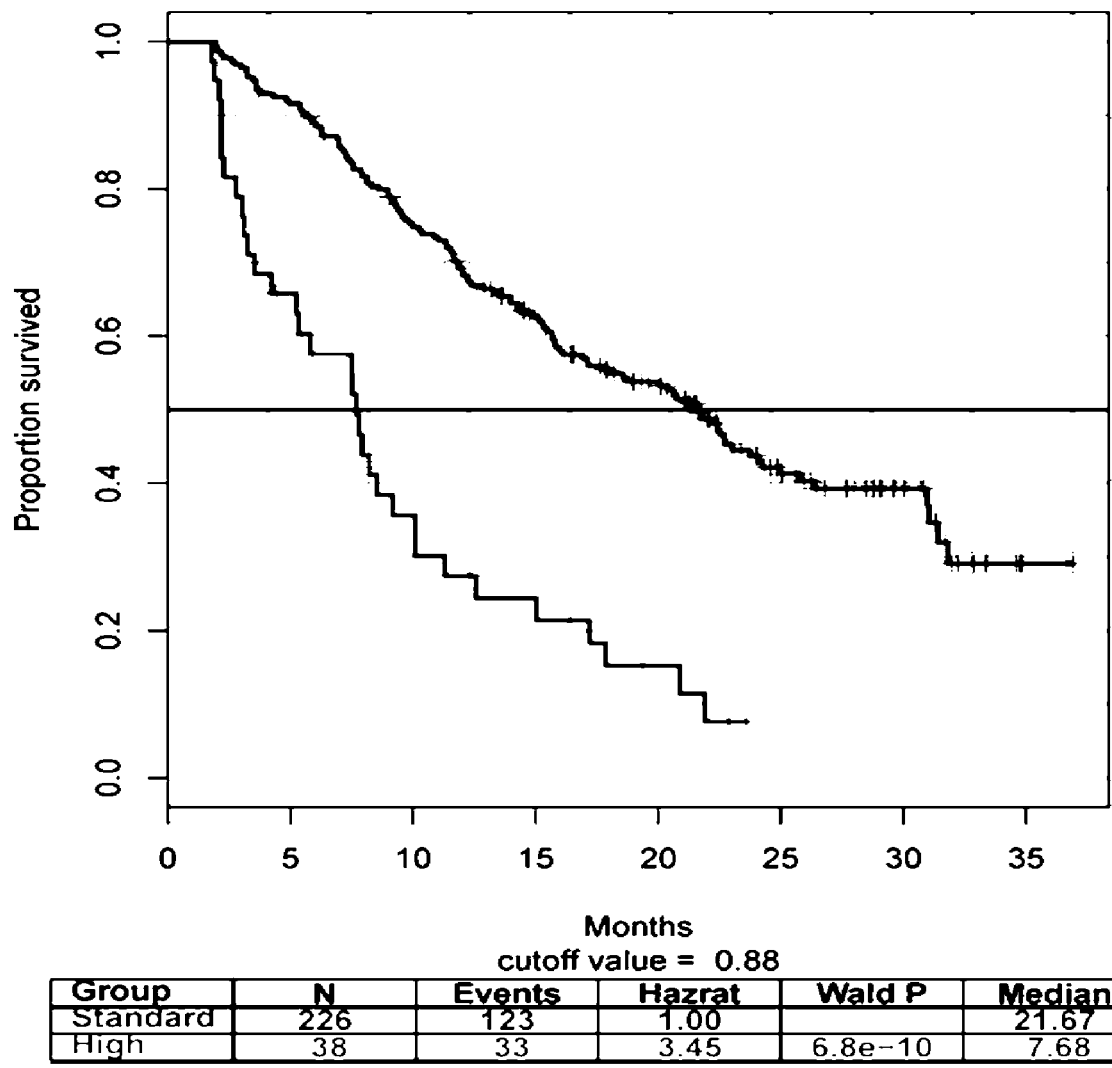

A dichotomizing cut-off threshold was based on the clinically relevant definition of high-risk patients as those patients who have an overall survival of less than 2 years. This amounted to a proportion of 21.7% in the training set and a cut-off value of 0.827. Within all four data sets TT2(n=351),[11] TT3(n=208),[11] MRC-IX(n=247)[14] and APEX(n=264),[12] the EMC-92-gene signature discriminated a high-risk group, which was significantly set apart from the standard-risk group (FIGS. 1A to 1D).

In datasets containing newly diagnosed patients, the EMC-92-gene signature selected a high-risk population of 17.7% on average, with a significantly shorter OS and hazard-ratios of 3.52 ($p=2.5 \times 10^{-8}=$; TT2), 2.7 ($p=0.07=^2$; TT3) and 2.38 ($p=3.6 \times 10^{-6}=$; MRC-IX). In the relapse setting, the EMC-92-gene signature also filtered out high-risk patients with a large hazard-ratio of 3.14 ($p=5.3 \times 10^{-9}=$; APEX). The proportion of high-risk patients in this latter study was lower compared to the MRC-IX and TT2 studies, but not significantly (15.9%, n=264 vs. 19.6%, n=; p=0.2) (Table 1.1).

In a multivariate covariant analysis, the EMC-92-gene signature was independent of most standard prognostic factors and clinical characteristics. Three datasets were available for this analysis: HOVON65/GMMG-HD4, APEX and MRC-IX. Multivariate analysis on the HOVON65/GMMG-HD4 study demonstrates that together with the EMC-92-gene signature, del(17p), $\beta_2$m[≥3.5 mg/L] and allogenic transplantation were significantly related to shorter survival, whereas WHO status [0] was found to be significantly related to longer survival. In the APEX, albumin level, ISS and IgG isotype were found to be significantly related. For the MRC-IX, mainly ISS related covariants were found. WHO[2], 1q gain and IGH split showed a clear contribution. IGH split indicates all patients with cytogenetic aberration of the IGH locus. Age had a small but significant hazard-ratio here. In all three datasets, the EMC-92-gene signature remained a strong predictor for survival after correction for available variables.

The samples in all four validation sets were assigned a molecular cluster label by the nearest neighbor classification. Logistic regression for association between the molecular clusters and high-risk outcome revealed a significant relation between high-risk classification and the MF, MS, PR and HY clusters.

Comparing the UAMS-17-gene and EMC-92-gene set in independent datasets (for example, TT3, MRC-IX and APEX), a significantly higher proportion of patients was classified as high-risk by the EMC-92-gene signature (p=0.009). Moreover, the estimated hazard-ratios (high-risk/standard-risk) were higher in the EMC-92-gene classifier with the exception of the TT3 study.

In the MRCIX study population, the EMC-92-gene classifier exclusively identified 31 patients correctly as high risk patients, which were missed by the UAMS-17-gene classifier (50% survival rate of 11, 24 and 51 months for the shared high risk group, intermediate high risk group and standard risk groups, respectively). Moreover, the UAMS-17-gene classifier exclusively identified 10 patients as high risk patients with a lower hazard ratio as compared to the 31 patients classified as high-risk by the EMC-92-gene classifier.

The superiority of the EMC-92-gene classifier was even clearer in the APEX population. Here, 24 patients were exclusively identified as high risk in the EMC-92-gene classifier, which were missed in the UAMS-17-gene classifier. These 24 patients formed a group whose overall survival after 20 months was 14% whereas the high risk population identified in both the EMC-92-gene and UAMS-17-gene classifier showed an overall survival of 25% after 20 months.

In addition, the UAMS-70-gene, MRC-IX-6-gene signature, GPI score, the Millennium and IFM signature were applied to the datasets. In a pair-wise multivariate analysis based on the pooled independent datasets, including two classifiers at a time and correcting for study and age, the EMC-92-gene classifier had the highest hazard ratios and lowest p values of all classifiers.

The intersection of high-risk patients between the EMC-92-gene and UAMS-17-gene classifiers was ~8% of the total population. About 14% of patients were classified as high-risk by either one of these classifiers. The intersecting high-risk group showed the largest differences compared to the intersecting standard-risk group as indicated by the hazard-ratios (HR=5.40; p=$3.1\times10^{-3}$; TT3), (HR=3.84; p=$5\times10^{-7}$; MRC-IX) and (HR=3.39; p=$1.9\times10^{-5}$; APEX). The 14% of patients uniquely classified as high-risk by either signature, showed an intermediate hazard-ratio. For the UAMS-17-gene high-risk group, this resulted in hazard-ratios of 4.08 (p=$7.6\times10^{-2}$), 1.92 (p=$7.7\times10^{-2}$) and 2.31 (p=$2.3\times10^{-2}$) for the TT3, MRX-IX and APEX. The EMC-92-gene high-risk group gave hazard-ratios of 0 (p=1.0 no events), 1.98 (p=$2.9\times10^{-34}$) and 3.21 (p=$1.6\times10^{-6}$) for the TT3, MRX-IX and APEX.

In clinical practice, prognosis of MM patients is mainly based on ISS-stage and interphase fluorescence in situ hybridization (FISH). Several chromosomal aberrations detected by FISH have prognostic implications.[25] Del(17p) is considered the most important, associated with unfavorable outcome and present in 9% of patients.[26, 27] Still 60% of patients with this deletion do not display a specific poor outcome.[28] The combination of chromosomal aberration, t(4;14), del(17p) and ISS have further delineated patients with a poor prognosis.[29]

Previously, in the UAMS classification, the MS, MF and PR clusters showed lower PFS and OS, whereas clusters HY, LB, CD-1 and CD-2 were associated with longer PFS and OS.[8] Here, the variability in PFS and OS in the GEP-based clusters of the HOVON65 classification was evaluated. VAD-treated patients demonstrate significant differences in PFS and OS between clusters with a clearly reduced survival for the MF subgroup, whereas in bortezomib-(PAD-) treated patients, no significant differences were found.

Bortezomib-based treatment has been shown to overcome certain adverse prognostic markers such as del(13q), resulting in better PFS and OS in patients with poor prognostic markers such as ISS-3, del(17p), and t(4;14).[16] Both chromosomal markers and the HOVON65 GEP-based classification vary with treatment and are not applicable for diagnosing high-risk patients accurately. Therefore, a high-risk GEP signature was developed.

Previous classifiers include the UAMS-17/70-gene and MRC-IX-6-gene classifiers, both capable of predicting in independent datasets.[11, 14] In contrast, the Millennium and the IFM signatures demonstrate less solid performance in independent validation sets.[12, 13]

The EMC-92-gene expression signature presented herein, is highly discriminative for patients with high-risk versus standard-risk MM across different (induction) regimes. Validation in UAMS TT2 (thalidomide-based),[17] TT3 (bortezomib-based),[18] and MRC-IX trial (thalidomide maintenance in both young and elderly patients)[19, 20] showed high performance in these independent test environments. This is true for both the continuous fit of the model, which is a goodness-of-fit indicator, as well as the dichotomized output into high-risk/standard-risk, which is a requirement for practical use in a clinical setting.

In multivariate analyses, the EMC-92-gene high-risk signature remains a strong predictor for early death. Still, there is strong evidence that ISS staging (serum albumin and $\beta_2$m levels) turns out to be another major contributor for explaining survival-related variance in the presence of the signature. Therefore, incorporating ISS into the signature could potentially lead to an even better prediction of survival.

Patients classified as high-risk are overrepresented within the molecular MF, MS and PR clusters and underrepresented within the HY cluster. This correlates well with previous data: HY represents hyperdiploid patients with a generally favorable prognosis; on the other hand, MS and MF represent patients with translocations t(4;14) and t(14;16/20), which are usually thought to have an unfavorable prognosis. Finally, PR represents the proliferation cluster, which was shown to be associated with poor prognosis.[8, 11, 15] In relation to this, pathway analysis of the EMC-92-gene signature demonstrated cell cycle regulation to be among the main functions found.

In the EMC-92-gene signature as well as the set of genes linked to survival in the univariate analysis, chromosomal location of 1q was highly enriched (Table 1) as was previously shown for the UAMS-17-gene signature.[11] Also, probe sets located on chromosome 4 are enriched. These probe sets were found to be scattered over the entire chromosome and not only at the distal end of the p arm where MMSET and FGFR3 are located. Chromosome 4 has previously not been considered a risk factor, but a low frequency of multiple gains and/or losses affecting this chromosome has been reported.[30]

The EMC-92-gene signature was compared in a multivariable analysis to the UAMS-17/70-gene, MRC-IX-6-gene, GPI score, IFM and Millennium classifiers. Three pooled datasets were formed from publicly available MM datasets, allowing an independent comparison of the signatures that were not trained on those datasets (R. Kuiper et al., Leukemia 2012, 1-8 incorporated herein by reference). The outputs from the signatures were input into a Cox proportional hazards model, see Table 2. In all three comparisons, the EMC-92-gene signature obtained the most significant hazard ratio (HR) and, thus, is the most relevant prognostic factor of all signatures (including the UAMS-70 from Signal Genetics).

TABLE 2

Comparison of EMC-92 with conventional tests (HR = hazard ratio)

| | Datasets pooled | Signature | HR | P-value |
|---|---|---|---|---|
| Comparison 1 | MRCIX + APEX + TT3 | SKY92[11] | 1.75 | 4.60E−04 |
| | | UAMS17[10] | 1.22 | 3.30E−01 |
| | | UAMS70[10] | 1.80 | 1.10E−03 |
| | | IFM15[12] | 1.25 | 9.10E−02 |
| Comparison 2 | APEX + TT2 + TT3 | SKY92 | 2.53 | 3.70E−09 |
| | | MRCIX6[13] | 1.50 | 4.10E−03 |
| | | IFM15 | 1.38 | 2.50E−02 |
| Comparison 3 | MRCIX + TT2 + TT3 | SKY92 | 2.95 | 5.60E−12 |
| | | Millennium100[14] | 0.81 | 1.30E−01 |
| | | IFM15 | 1.13 | 4.00E−01 |

The EMC-92-gene signature turns out to have the best dichotomized performance on its validation sets. Moreover, in comparison to other classifiers, the proportion of high-risk patients is higher. One would expect that differences between high-risk and standard-risk become less pronounced as the high-risk proportion increases. It should be mentioned that even at this high proportion, differences in survival time are larger for the EMC-92 as compared to other classifiers selecting smaller risk groups.

In a multivariate analysis combining the signatures, the EMC-92-gene signature had the strongest discriminative ability.

In conclusion, a high-risk signature highly discriminative for patients with high-risk versus standard-risk MM, irrespective of treatment regime, age and relapse setting was developed. Use of this signature in the clinical setting may lead to a more informed treatment choice and potentially better outcome for the patient.

In conclusion, this study concerns the development of a robust high-risk signature, incorporates most known prognostic markers, clinical, cytogenetic and GEP based, and shows the developed EMC-92-gene signature to be the strongest independent prognostic marker for poor survival known. This EMC-92-gene signature is able to select out a high-risk group of MM patients for whom in the future alternative, more intensive treatments should be sought.

Hence, the disclosure relates to a method for determining the disease outcome or the prognosis of a patient diagnosed with multiple myeloma by classifying the patient into a high risk or a low risk category, the method comprising the steps of:
  a) providing a gene chip comprising probes for the detection of at least the 92-gene set according to Table 1,
  b) contacting the gene chip with a sample comprising mRNA from a patient,
  c) determining the expression levels of the 92-gene set in the sample,
  d) normalizing the expression levels using mean/variance normalization in order to obtain the normalized expression value,
  e) multiply the normalized expression value with the beta value according to Table 1 to obtain the calculated value for an individual probe,
  f) determine an EMC-92 score by summation of the calculated values of the individual probes,
  wherein an EMC-92 score above a predetermined threshold indicates that the patient is to be classified in the high-risk category and a score at or below the threshold indicates that the patient is to be classified in the low-risk category.

As further detailed herein, a preferred threshold value is at least 0.75, especially preferred is a threshold value of 0.827.

In summary, the generation and validation of the EMC-92-gene signature, which was based on the HOVON65/GMMG-HD4 clinical trial, is reported herein. Conventional prognostic markers such as ISS stage and adverse cytogenetics have been augmented by signatures based on gene expression in order to increase accuracy in outcome prediction in MM. More accurate prognosis may lead to the development of treatment schedules that are specifically aimed at improving survival of high-risk MM patients.

For clinical relevance, a signature must have both the ability to separate risk groups as clearly as possible and to predict stable groups of relevant size. The EMC-92-gene signature meets both criteria. In all validation sets, a high-risk group of patients can be significantly determined and the proportion of high-risk patients is stable across the validation sets. The validation sets represent different drug regimens, including thalidomide (MRC-IX, TT2) and bortezomib (APEX, TT3). Also, the signature is relevant to both transplant-eligible (for example, TT3) and non-transplant-eligible patients (subset of MRC-IX), as well as newly diagnosed (for example, TT2) and relapsed patients (APEX). In contrast, the predictions of the IFM-15 and MILLENNIUM-100 signatures in the validation sets fail to reach significance in independent data sets such as MRC-IX and TT3.

In conclusion, a risk signature that is highly discriminative for patients with high-risk vs standard-risk MM, irrespective of treatment regime, age and relapse setting, has been developed. Use of this signature in the clinical setting may lead to a more informed treatment choice and potentially better outcome for the patient.

EXAMPLES

Example 1: Patients

Five previously described datasets were used, of which both survival as well as GEPs of purified plasma cells obtained from bone marrow aspirates of myeloma patients, were available. These are HOVON65/GMMG-HD4 (N=320) (GSE19784),[9] Total Therapy 2 (TT2) (n=351),[11] TT3 (n=208) (GSE2658),[11] MRC-IX (n=247) (GSE15695),[14] and APEX (n=264) (GSE9782).[12]

The HOVON65/GMMG-HD4 data was used as a training set. This multicenter trial compared the efficacy of bortezomib (PAD) to standard treatment (VAD) in newly diagnosed patients. Patients were randomized to induction treatment with three VAD or PAD cycles,[16] for a total of 290 patients, both follow-up and GEPs were available.[9]

The other four independent datasets were used as validation. Two datasets, TT2 and TT3, were derived from clinical trials performed in newly diagnosed patients, both treated with a complex regimen. The first was a randomized prospective treatment trial in which patients were randomly assigned to receive or not to receive thalidomide during all phases of treatment.[17] The latter was carried out by the same group according to the same regimen but with the addition of bortezomib to the thalidomide arm.[18] TT3 is a very small set with only 15 OS events but is included here for completeness.

The MRC-IX trial included both younger and older newly diagnosed patients. For younger patients, treatment consisted of induction with vincristine or no vincristine followed by transplantation. Older patients were treated initially with a thalidomide-vs. melphalan-based treatment. Maintenance for both young and old patients was a comparison of thalidomide vs. no thalidomide.[19, 20] The trial and dataset denoted here as APEX consisted of the three trials APEX, SUMMIT and CREST. These trials aimed at testing the efficacy of bortezomib in relapse cases.[21-23]

The IFM dataset on which the IFM signature was based has not been evaluated due to an incompatible GEP platform.[13]

Example 2: Gene Expression Analysis

Two types of Affymetrix gene expression platforms were used. The Affymetrix GENECHIP® Human Genome U133 Plus 2.0 Array was used in the HOVON65/GMMG-HD4, TT2, TT3 and MRC-IX whereas Affymetrix HG U133 A/B chips was used in the APEX study. To allow for validation across different studies, only probe sets present on both platforms were included. A lower probe set expression boundary was set to the 5% lowest expression for the bioB hybridization controls in the HOVON65/GMMG-HD4 set. Probe sets with a lower expression in ≥95% of the HOVON65/GMMG-HD4 patients were excluded. All data were MASS normalized, $\log_2$ transformed and mean-variance scaled.

The HOVON65/GMMG-HD4 molecular classification was performed previously.[9] To assign a cluster label to new validation samples, a Euclidean nearest neighbor algorithm was used with HOVON65/GMMG-HD4 being the reference set.

The HOVON65/GMMG-HD4 was used as a training set for building a GEP-based survival classifier. The model was built using a Supervised Principal Component Analysis (SPCA) framework. All calculations were performed in the R statistical environment using the survival package for survival analysis. The maxstat package was used to determine the optimal cut-off value for high-risk.

Data were analyzed using Ingenuity Pathway Analysis (INGENUITY SYSTEMS®, on the World-Wide Web at Ingenuity.com). Both the gene set corresponding to the SPCA-based survival classifier as well as the gene set generated by the initial univariate ranking (FDR<10%) were analyzed. Probe sets present in both the HG U133 Plus 2.0 and A/B platforms were used as a reference. P-values were derived from right-tailed Fisher exact tests corrected for multiple testing using Benjamini Hochberg correction.

Example 3: Comparison with Published Gene Signatures

The performance of the EMC-92-gene signature in relation to available GEP-based prognostic signatures for OS in MM was evaluated. To this end, the following signatures were evaluated: UAMS-70, UAMS-17, UAMS-80, IFM-15, gene proliferation index (GPI-50), MRC-IX-6 and MILLENNIUM-100.

Figure 2:
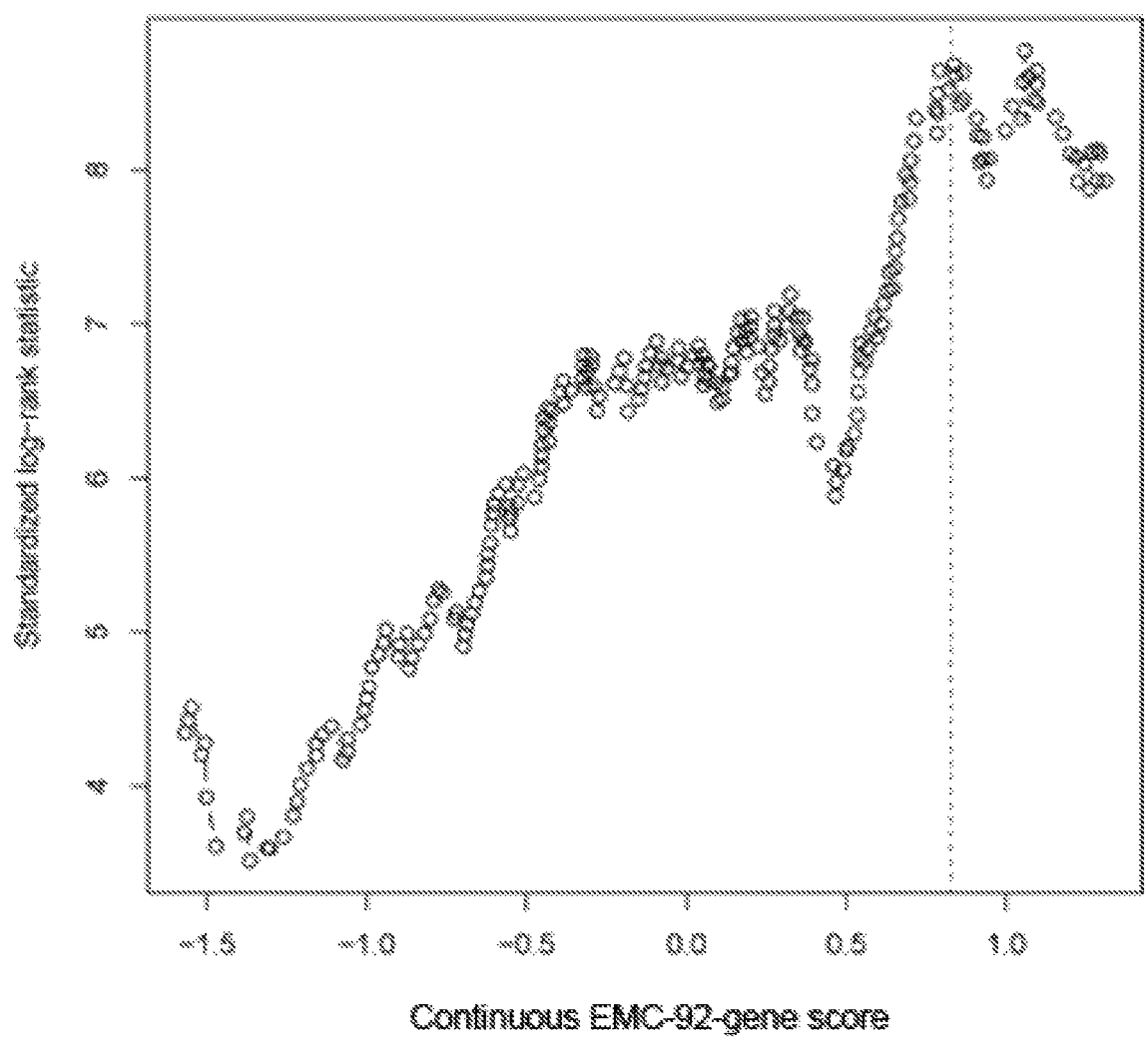
FIG. 2: Relation between threshold and log-rank performance of the EMC-92 signature in the HOVON-65/GMMG-HD4 OS. The model has an optimal performance for thresholds of at least 0.75. A cut-off for high-risk was based on defining high-risk as having an OS of <2 years within the training set, which corresponded to a threshold of 0.827.

These signatures were evaluated as continuous variables as well as using the cut-off values as published (FIG. 2 and FIGS. 2A-2E in reference 31, and Supplemental Documents A and B in reference 31). Overall, the performance of the EMC-92-gene signature was found to be robust, consistent, which compares favorably with previously published signatures. Specifically, the EMC-92, UAMS, MRC-IX and GPI-50 signatures demonstrated significance in all validation sets tested both for the dichotomized and for the continuous values of the signatures. Significance was reached in three out of five studies for the IFM-15 signature using a dichotomized model, whereas the MILLENNIUM-100 signature had significant performance in the dichotomized model in one out of four independent studies. Thus, performance was less robust for the IFM-15 and MILLENNIUM-100 signatures. Although the proliferation index GPI-50 was found to be significant in all validation sets tested, the proportion of high-risk patients was much lower compared with the proportion found using either the EMC-92 or the UAMS-80 signatures. Ranked, weighted high-risk proportions are GPI: 10.0%, UAMS-17: 12.4%, UAMS-70: 13.0%, MRC-IX-6: 13.3%, EMC-92: 19.1% and UAMS-80: 23.4%. To determine which signature best explained the observed survival, pair-wise comparisons were performed. For every comparison, the EMC-92 was the strongest predictor for OS tested in an independent environment (FIG. 3 and Supplemental Table S9 in reference 31).

Example 4: Combined Risk Classifiers

The performance of the EMC-92-gene signature was in line with the UAMS signatures, although they were derived from quite different patient populations. The intersection of high-risk patients between the EMC-92 and UAMS-70 signatures was ~8% of the total population on the pooled data sets that were independent of both the training set and the UAMS-70 training set (that is, MRC-IX, TT3 and APEX; Supplemental Table S11 in reference 31). Approximately 13% of patients were classified as high-risk by either one of these signatures. The intersecting high-risk group had the highest HR as compared with the intersecting standard-risk group (HR=3.87, 95% CI=2.76-5.42, P=3.6×10-15). Patients classified as high-risk by either signature showed an intermediate risk, that is, with a HR of 2.42, 95% CI=1.76-3.32, for the EMC-92-gene signature (P=5.1×10-8) and a HR of 2.22, 95% CI=1.20-4.11, for the UAMS-70 signature (P=1.1×10-2; Supplemental Table S12 in reference 31).

Example 5: EMC-92-Gene Signature and FISH

To compare the high-risk populations composition as defined by the EMC-92 and the UAMS-70 signatures, cytogenetic aberration frequencies in both populations were determined using an independent set for which cytogenetic variables were known, that is, MRC-IX (FIG. 4 and Supplemental Table S13 in reference 31). As expected, poor prognostic cytogenetic aberrations 1q gain, del(17p), t(4; 14), t(14;16), t(14;20) and del(13q) were enriched in the high-risk populations (FIG. 5 in reference 31), whereas the standard-risk cytogenetic aberrations such as t(11;14) were diminished in the high-risk populations. In contrast, only 15% (6 out of 39) of MRC-IX cases with high-risk status as determined by the EMC-92-gene signature showed absence of any poor prognostic cytogenetic aberrations, as opposed to 44% (74 out of 168) in standard-risk cases (P=1.8×10-3). Similarly, of the UAMS-70-defined high-risk patients 4% (1 out of 23) did not have any poor prognostic cytogenetics, whereas of the UAMS-70 defined standard risk patients, this proportion was 43% (79 out of 183) (P=5.3×10-3).

The following references are incorporated herein by reference. Their contents should be regarded as an integral part of this application.

REFERENCES

1. Greipp P. R., J. San Miguel, B. G. Durie, J. J. Crowley, B. Barlogie, J. Blade, et al. International staging system for multiple myeloma. *J. Clin. Oncol.* 2005 May 20; 23(15): 3412-20.
2. Bergsagel P. L., W. M. Kuehl. Molecular Pathogenesis and a Consequent Classification of Multiple Myeloma. *J. Clin. Oncol.* 2005 Sep. 10; 23(26):6333-8.
3. Fonseca R., C. S. Debes-Marun, E. B. Picken, G. W. Dewald, S. C. Bryant, J. M. Winkler et al. The recurrent IgH translocations are highly associated with nonhyperdiploid variant multiple myeloma. *Blood* 2003 Oct. 1; 102(7):2562-7.
4. Fonseca R., J. D. Hoyer, P. Aguayo, S. M. Jalal, G. J. Ahmann, S. V. Rajkumar et al. Clinical significance of the translocation (11;14)(q13;q32) in multiple myeloma. *Leuk. Lymphoma.* 1999; 35(5-6):599-605.
5. Keats J. J., T. Reiman, C. A. Maxwell, B. J. Taylor, L. M. Larratt, and M. J. Mant et al. In multiple myeloma, t(4;14)(p16;q32) is an adverse prognostic factor irrespective of FGFR3 expression. *Blood* 2003 Feb. 15; 101(4): 1520-9.
6. Avet-Loiseau H., F. Malard, L. Campion, F. Magrangeas, C. Sebban, and B. Lioure et al. Translocation t(14;16) and multiple myeloma: is it really an independent prognostic factor? *Blood* 2011 Feb. 10; 117(6):2009-11.
Cremer F. W., J. Bila, I. Buck, M. Kartal, D. Hose, C. Ittrich et al. Delineation of distinct subgroups of multiple myeloma and a model for clonal evolution based on interphase cytogenetics. *Genes, Chromosomes & Cancer* 2005 October; 44(2):194-203.
8. Zhan F., Y. Huang, S. Colla, J. P. Stewart, I. Hanamura, S. Gupta et al. The molecular classification of multiple myeloma. *Blood* 2006 Sep. 15; 108(6):2020-8.
9. Broyl A., D. Hose, H. Lokhorst, Y. de Knegt, J. Peeters, A. Jauch et al. Gene expression profiling for molecular classification of multiple myeloma in newly diagnosed patients. *Blood* 2010 Oct. 7; 116(14):2543-53.
10. Chng W. J., W. M. Kuehl, P. L. Bergsagel, and R. Fonseca. Translocation t(4;14) retains prognostic significance even in the setting of high-risk molecular signature. *Leukemia* 2008 February; 22(2):459-61.
11. Shaughnessy J. D., Jr., F. Zhan, B. E. Burington, Y. Huang, S. Colla, I. Hanamura et al. A validated gene expression model of high-risk multiple myeloma is defined by deregulated expression of genes mapping to chromosome 1. *Blood* 2007 Mar. 15; 109(6):2276-84.
12. Mulligan G., C. Mitsiades, B. Bryant, F. Zhan, W. J. Chng, S. Roels et al. Gene expression profiling and correlation with outcome in clinical trials of the proteasome inhibitor bortezomib. *Blood* 2007 Apr. 15; 109(8): 3177-88.
13. Decaux O., L. Lode, F. Magrangeas, C. Charbonnel, W. Gouraud, P. Jezequel, et al. Prediction of survival in multiple myeloma based on gene expression profiles reveals cell cycle and chromosomal instability signatures in high-risk patients and hyperdiploid signatures in low-risk patients: a study of the Intergroupe Francophone du Myelome. *J. Clin. Oncol.* 2008 Oct. 10; 26(29):4798-805.
14. Dickens N. J., B. A. Walker, P. E. Leone, D. C. Johnson, J. L. Brito, A. Zeisig et al. Homozygous deletion mapping in myeloma samples identifies genes and an expression signature relevant to pathogenesis and outcome. *Clin. Cancer Res.* 2010 Mar. 15; 16(6):1856-64.
15. Hose D., T. Reme, T. Hielscher, J. Moreaux, T. Messner, A. Seckinger et al. Proliferation is a central independent prognostic factor and target for personalized and risk-adapted treatment in multiple myeloma. *Haematologica* 2011 January; 96(1):87-95.
16. Sonneveld P., I. Schmidt-Wolf, B. van der Holt, L. E. Jarari, U. Bertsch, H. Salwender et al. HOVON-65/GMMG-HD4 Randomized Phase III Trial Comparing Bortezomib, Doxorubicin, Dexamethasone (PAD) vs VAD Followed by High-Dose Melphalan (HDM) and Maintenance with Bortezomib or Thalidomide In Patients with Newly Diagnosed Multiple Myeloma (MM). *Blood* 2010 Nov. 19; 116(21):40.
17. Barlogie B., M. Pineda-Roman, F. van Rhee, J. Haessler, E. Anaissie, K. Hollmig et al. Thalidomide arm of Total Therapy 2 improves complete remission duration and survival in myeloma patients with metaphase cytogenetic abnormalities. *Blood* 2008 Oct. 15; 112(8):3115-21.
18. Pineda-Roman M., M. Zangari, J. Haessler, E. Anaissie, G. Tricot, F. van Rhee, et al. Sustained complete remissions in multiple myeloma linked to bortezomib in total therapy 3: comparison with total therapy 2. *British journal of haematology* 2008 March; 140(6):625-34.
19. Morgan G. J., F. E. Davies, W. M. Gregory, S. E. Bell, A. J. Szubert, N. Navarro-Coy et al. Thalidomide Maintenance Significantly Improves Progression-Free Survival (PFS) and Overall Survival (OS) of Myeloma Patients When Effective Relapse Treatments Are Used: MRC Myeloma IX Results. *Blood* 2010 Nov. 19; 116(21):623.
20. Morgan G. J., F. E. Davies, R. G. Owen, A. C. Rawstron, S. Bell, K. Cocks et al. Thalidomide Combinations Improve Response Rates; Results from the MRC IX Study. *Blood* 2007 Nov. 16; 110(11):3593-.
21. Jagannath S., B. Barlogie, J. Berenson, D. Siegel, D. Irwin, P. G. Richardson et al. A phase 2 study of two doses of bortezomib in relapsed or refractory myeloma. *British journal of haematology* 2004 October; 127(2):165-72.
22. Richardson P. G., B. Barlogie, J. Berenson, S. Singhal, S. Jagannath, D. Irwin et al. A phase 2 study of bortezomib in relapsed, refractory myeloma. *The New England journal of medicine,* 2003 Jun. 26; 348(26):2609-17.
23. Richardson P. G., P. Sonneveld, M. W. Schuster, D. Irwin, E. A. Stadtmauer, T. Facon et al. Bortezomib or high-dose dexamethasone for relapsed multiple myeloma. *The New England journal of medicine* 2005 Jun. 16; 352(24):2487-98.
24. Bair E., T. Hastie, D. Paul, and R. Tibshirani. Prediction by Supervised Principal Components. *J. Amer. Statistical Assoc.* 2006 Mar. 1; 101(473):119-37.
25. Avet-Loiseau H., F. Magrangeas, P. Moreau, M. Attal, T. Facon, K. Anderson et al. Molecular Heterogeneity of Multiple Myeloma: Pathogenesis, Prognosis, and Therapeutic Implications. *J. Clin. Oncol.* 2011 May 10; 29(14): 1893-7.
26. Avet-Loiseau H., M. Attal, P. Moreau, C. Charbonnel, F. Garban, C. Hulin et al. Genetic abnormalities and survival in multiple myeloma: the experience of the Intergroupe Francophone du Myelome. *Blood* 2007 Apr. 15; 109(8): 3489-95.

27. Fonseca R., P. L. Bergsagel, J. Drach, J. Shaughnessy, N. Gutierrez, A. K. Stewart et al. International Myeloma Working Group molecular classification of multiple myeloma: spotlight review. *Leukemia* 2009 December; 23(12):2210-21.
28. Avet-Loiseau H., X. Leleu, M. Roussel, P. Moreau, C. Guerin-Charbonnel, D. Caillot et al. Bortezomib plus dexamethasone induction improves outcome of patients with t(4;14) myeloma but not outcome of patients with del(17p). *J. Clin. Oncol.* 2010 Oct. 20; 28(30):4630-4.
29. Neben K., A. Jauch, U. Bertsch, C. Heiss, T. Hielscher, and A. Seckinger et al. Combining information regarding chromosomal aberrations t(4;14) and del(17p13) with the International Staging System classification allows stratification of myeloma patients undergoing autologous stem cell transplantation. *Haematologica* 2010 July; 95(7): 1150-7.
30. Carrasco D. R., G. Tonon, Y. Huang, Y. Zhang, R. Sinha, and B. Feng et al. High-resolution genomic profiles define distinct clinico-pathogenetic subgroups of multiple myeloma patients. *Cancer Cell* 2006; 9(4):313-25.
31. Kuiper, R. et al. *Leukemia* 2012, 1-8 advance on line publication, 22 Jun. 2012; doi:10.1038/leu.2012.127.

What is claimed is:

1. A method of gene expression profiling of a multiple myeloma, the method comprising:

detecting an mRNA level in a sample for each of the genes in a set consisting of 92 genes;

wherein the 92 genes in the gene set are SLC30A7, AK2, SYF2, S100A6, NUF2, DARS2, ARPC5, DTL, ANGEL2, LBR, TARBP1, GGPS1, LTBP1, FAM49A, MCM6, ACVR2A, GRB14, ITGA6, DHRS9, STAT1, SPATS2L, BCS1L, SFMBT1, ARL8B, POLQ, MCM2, CCRL1, SEC62, GABRA4, PGM2, NCAPG, FGFR3, SEPT11, AIMP1, CENPE, IL7R, DHFR, SAR1B, PCDHB7, ATP6V0E1, MCM3, TUBB, MARCKS, SLC17A5, NCUBE1, SUN1/GET4, DNAJB9, RAB2A, TRAM1, ZNF252, HNRNPK, MRPL41, ZWINT, FANCF, EHBP1L1, C11orf85, PPP2R1B, ROBO3, C1S, ESPL1, ITM2B, ZBTB25, NPC2, ATPBD4, C15orf38, FANCI, SMG1, DYNLRB2, TMEM97, SPAG5, TOP2A, BIRC5, C18orf10, TSPAN16, RPS28, RPS11, NOP56, FTL, CDH22, DONSON, PFKL, ST13, DUX4, RPS4X, KIF4A, HMGN5, HMGB3, MAGEA6, the gene at chromosome 8p12 detectable with probe 208232 x at, the gene at chromosome 11p14.1 detectable with probe 243018 at, and the gene at chromosome 11q24.3 detectable with probe 238780 s at, and wherein the sample comprises plasma cells.

* * * * *